United States Patent [19]

Bianchini et al.

[11] Patent Number: 4,933,326

[45] Date of Patent: Jun. 12, 1990

[54] OLIGOSACCHARIDES OBTAINED BY HEPARIN DEPOLYMERIZATION HAVING ANTIATHEROSCLEROTIC ACTIVITY

[75] Inventors: Pietro Bianchini; Giuseppe Mascellani, both of Corlo, Italy

[73] Assignee: Opocrin S.p.A., Corlo, Italy

[21] Appl. No.: 247,154

[22] Filed: Sep. 21, 1988

Related U.S. Application Data

[63] Continuation-in-part of Ser. No. 921,332, Oct. 21, 1986, Pat. No. 4,791,195, which is a continuation-in-part of Ser. No. 582,933, Feb. 23, 1984, Pat. No. 4,629,699.

[30] Foreign Application Priority Data

Mar. 8, 1983 [IT] Italy .................. 40021 A/83

[51] Int. Cl.$^5$ ................. A61K 31/725; C08B 37/10
[52] U.S. Cl. ......................... 514/56; 536/21; 514/822
[58] Field of Search ............. 536/21; 514/56, 822

[56] References Cited

U.S. PATENT DOCUMENTS

| | | | |
|---|---|---|---|
| 4,303,651 | 12/1981 | Lindahl et al. | 536/21 |
| 4,351,938 | 9/1982 | Barnett | 536/21 |
| 4,500,519 | 2/1985 | Lormeau et al. | 536/21 |

*Primary Examiner*—John W. Rollins
*Attorney, Agent, or Firm*—Bucknam and Archer

[57] ABSTRACT

Heparin fractions which are a mixture of oligosaccharides containing 6–12 monosaccharides are described. The oligosaccharides contain reducing end groups composed of iduronic acid 2-sulfate or glucosamine N, 6-disulfate. The end group monosaccharides contain the reducing anomeric carbons. The $SO_3^-/COO^-$ ratio is essentially the same as in heparin. The method of preparation is a depolymerization initiated by free radicals. One fraction is a heparin fragment with a molecular weight (MWw) of 2,100 daltons (+10%). The compound contains 6–8 monosaccharides, has the same $SO_3^-/COO^-$ ratio as the parent heparin and has platelet anti-aggregating activity, arterial and venous antithrombotic action, fibrinolytic and antiatherosclerotic activity. It exhibits poor anti factor Xa activity and no anticoagulant action.

7 Claims, 6 Drawing Sheets

Figure 1:
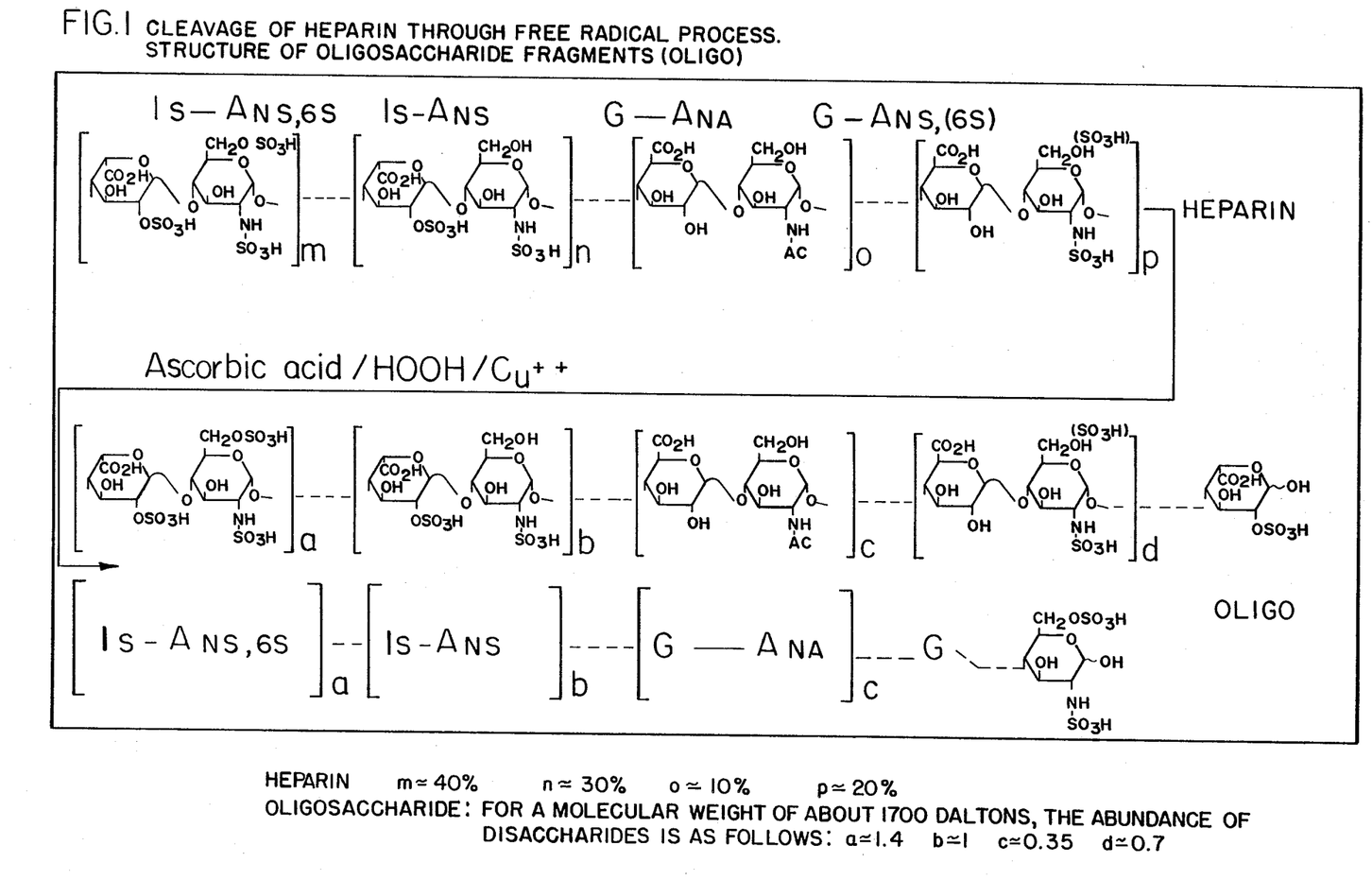

FIG.1 CLEAVAGE OF HEPARIN THROUGH FREE RADICAL PROCESS. STRUCTURE OF OLIGOSACCHARIDE FRAGMENTS (OLIGO)

HEPARIN  m≃40%  n≃30%  o≃10%  p≃20%
OLIGOSACCHARIDE: FOR A MOLECULAR WEIGHT OF ABOUT 1700 DALTONS, THE ABUNDANCE OF DISACCHARIDES IS AS FOLLOWS: a≃1.4  b≃1  c≃0.35  d≃0.7

Figure 2:
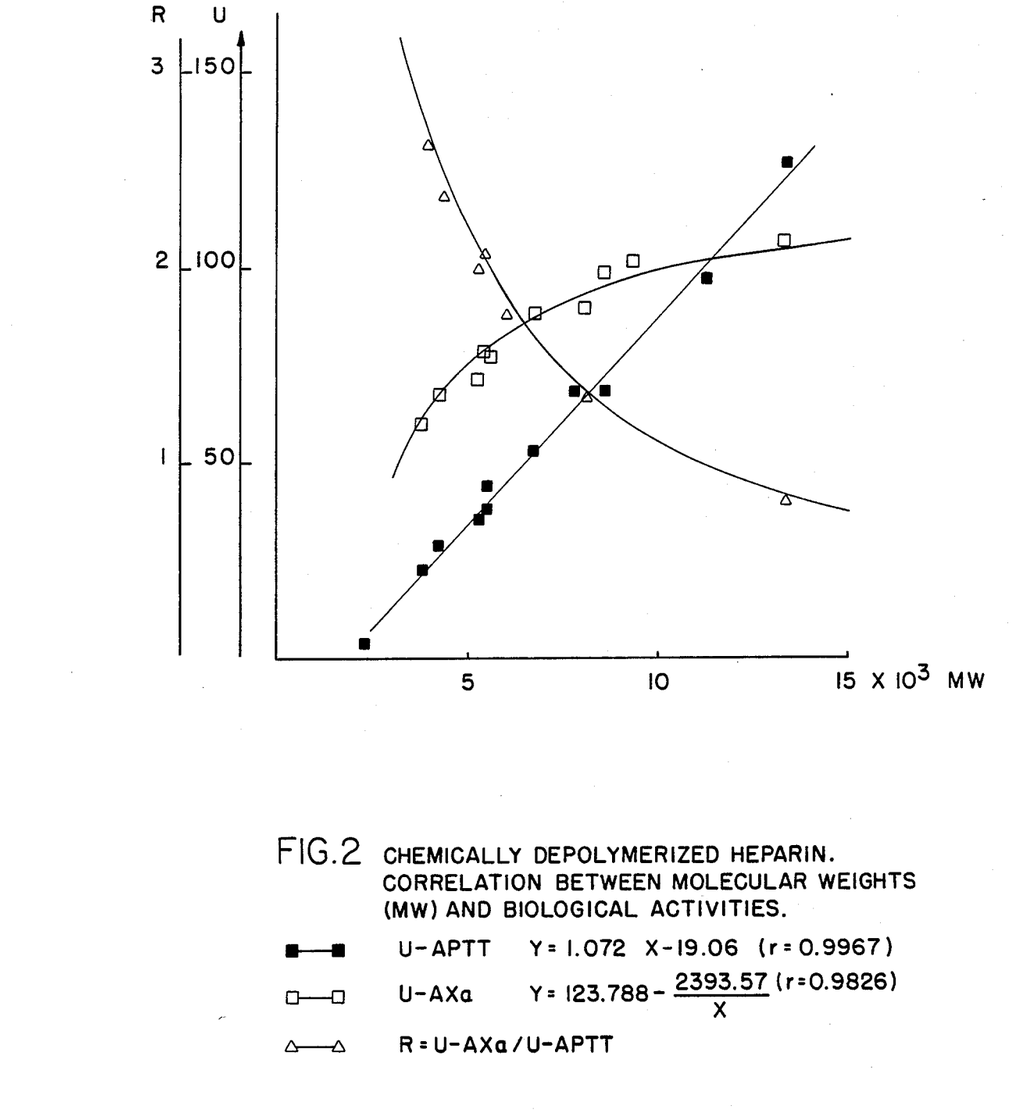

FIG.2 CHEMICALLY DEPOLYMERIZED HEPARIN. CORRELATION BETWEEN MOLECULAR WEIGHTS (MW) AND BIOLOGICAL ACTIVITIES.

■—■ U-APTT $Y = 1.072 X - 19.06$ (r = 0.9967)

□—□ U-AXa $Y = 123.788 - \dfrac{2393.57}{X}$ (r = 0.9826)

△—△ R = U-AXa/U-APTT

Figure 3:
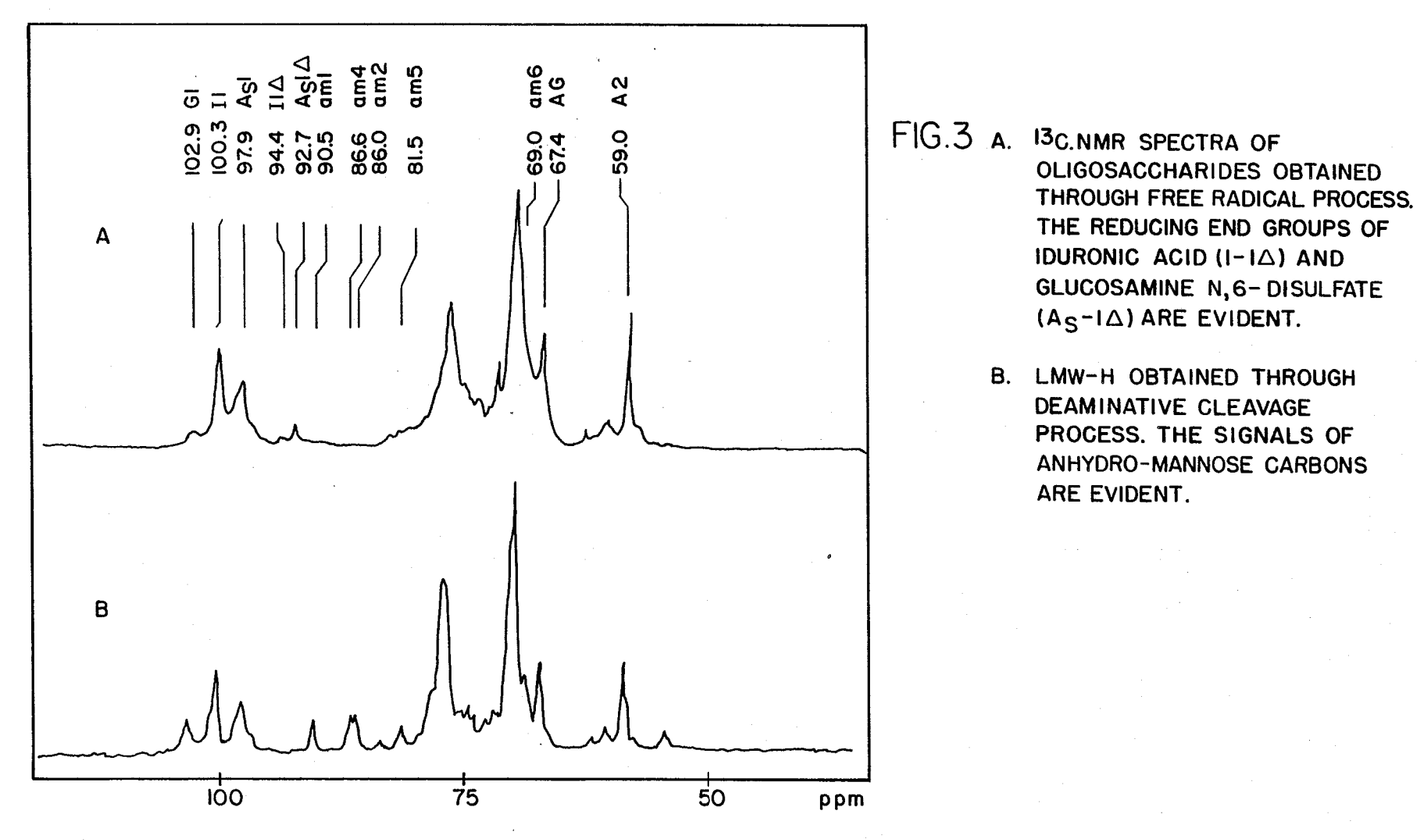

FIG. 3. A. 13C.NMR SPECTRA OF OLIGOSACCHARIDES OBTAINED THROUGH FREE RADICAL PROCESS. THE REDUCING END GROUPS OF IDURONIC ACID (I-IΔ) AND GLUCOSAMINE N,6-DISULFATE ($A_S$-IΔ) ARE EVIDENT.

B. LMW-H OBTAINED THROUGH DEAMINATIVE CLEAVAGE PROCESS. THE SIGNALS OF ANHYDRO-MANNOSE CARBONS ARE EVIDENT.

Figure 4:
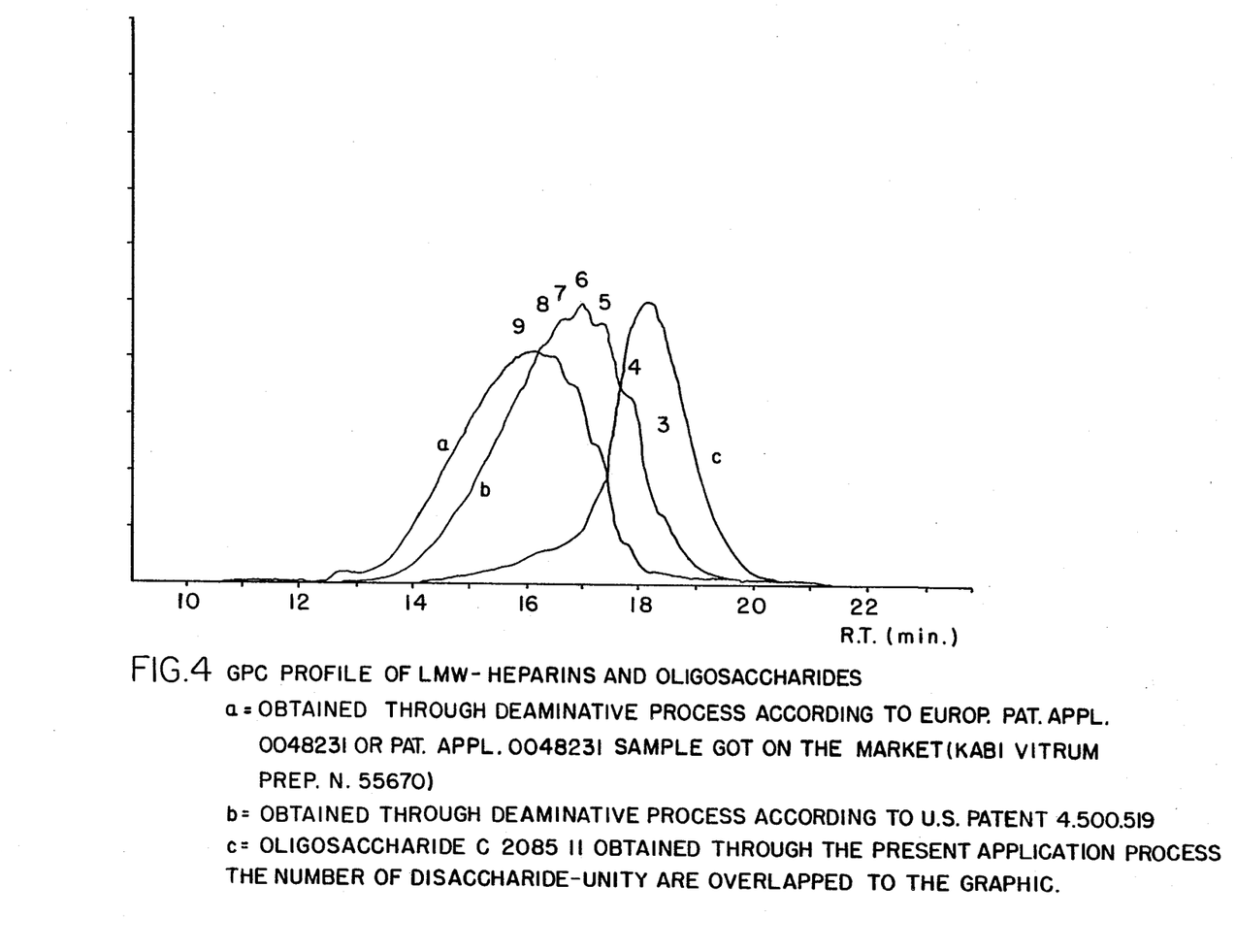

FIG. 4 GPC PROFILE OF LMW-HEPARINS AND OLIGOSACCHARIDES a = OBTAINED THROUGH DEAMINATIVE PROCESS ACCORDING TO EUROP. PAT. APPL. 0048231 OR PAT. APPL. 0048231 SAMPLE GOT ON THE MARKET (KABI VITRUM PREP. N. 55670)

b = OBTAINED THROUGH DEAMINATIVE PROCESS ACCORDING TO U.S. PATENT 4.500.519 c = OLIGOSACCHARIDE C 2085 II OBTAINED THROUGH THE PRESENT APPLICATION PROCESS THE NUMBER OF DISACCHARIDE-UNITY ARE OVERLAPPED TO THE GRAPHIC.

FIG.6

OLIGOSACCHARIDES OBTAINED BY HEPARIN DEPOLYMERIZATION HAVING ANTIATHEROSCLEROTIC ACTIVITY

This application is a continuation-in-part application of U.S. Ser. No. 921,332 filed Oct. 21, 1986, now U.S. Pat. No. 4,791,195, which was a Continuation-in-part of U.S. Pat. No. 582,933 filed Feb. 23, 1984, now U.S. Pat. No. 4,629,699. This invention regards heparin oligosaccharide fractions of molecular weight ranging from 3570 to 2100 and a fraction of 1700 daltons, which lack anticoagulant activity and have no affinity for antithrombin III (AT III) and which exhibit valuable biological activities such as antiatherosclerotic activity in vivo, also by oral administration route, inhibition of platelet aggregation, blocking action on spontaneous muscular contraction connected with inhibition of proliferation of subendothelial smooth muscle cells. This invention also concerns a chemical process for the preparation of these very low molecular weight fractions of heparin.

Individual oligosaccharides and olisaccharide fractions which are composed of a mixture of oligosaccharides, derived from heparin, are known to exhibit valuable antithrombotic activity associated with a relatively low anticoagulant activity as measured by global tests (APTT assay and pharmacopoeial assay). However, the known processes for the depolymerization of heparin have given fractions having a molecular weight lower than heparin but with structural characteristics different from the native heparin.

Surprisingly, the oligosaccharides and/or oligosaccharide fractions obtained by the process of this application have been found to maintain the structural integrity of native heparin. Further, the oligosaccharides and oligosaccharide fractions according to the present invention exhibit an antithrombotic activity on venous as well as on, mainly, arterial thrombosis. This antithrombotic activity is not AT III-dependent. Besides, they inhibit the proliferation of subendothelial smooth muscle cells. All the above activities place these compounds among the antiatherosclerotic drugs.

Many processes of heparin depolymerization have been described. They are based on different and peculiar either chemical or enzymatic reactions. The compounds which are obtained by these processes are characterized by as many structural peculiarities which distinguish one compounds from the others and from those of this invention.

Many depolymerization processes take place in acidic medium and exploit deaminative cleavage with nitrous acid. U.S. Pat. No. 4,303,651 claims an oligosaccharidic fraction having 14-18 sugar units (molecular weight: about 3600-4800 Daltons), obtained by deaminative cleavage with nitrous acid (Tab. I, reaction III) wherein the main component is the disaccharide unit: L-iduronosyl-2-0-sulfate-N-sulfo-D-glucosamine 6-0-sulfate and where unsulfated L-iduronic acid is in a 3-5 sugar unit position as regards unreducing terminal.

Such an oligosaccharide can be obtained also by depolymerization with Sodium periodate (Tab. I, reaction IV).

The U.S. Pat. Nos. 4,500,519 and 4,351,938 claim oligosaccharides which are obtained by heparin depolymerization with nitrous acid and have reducing terminals composed of anhydromannose which can be reduced to anhydromannitol or oxidized to D-mannonic acid, which are the final stage of re-arrangement of N-sulfate-D-glucosamine 6-0-sulfate (Tab. I, reaction III).

The U.S. Pat. Nos. 4,401,662 and 4,474,770 claim an oligosaccharide having a strong antithrombotic activity, which is composed of not more than 8 saccharidic units with very high affinity for antithrombin III (AT III), and very high inhibiting effect on activated factor X (up to 2000 U/mg). This oligosaccharide is obtained by heparin depolimerization with nitrous acid (Tab. I, reaction III) or with heparinase (Tab. I, reaction II). Its structure, besides, contains glucosamine having —O—$SO_3^-$ in position 3.

In the above-mentioned patents a depolymerization based on a cleavage involving only the bond between aminosugar and uronic acid has been described. Thus, the obtained oligosaccharide is always composed of a whole number of disaccharides and, where the cleavage takes place, a N-desulfation from the aminosugar cannot be avoided.

The other alternative depolymerization process by periodate oxidation described in Example 2 of U.S. Pat. No. 4,303,651 produces non-reducing end groups, since it splits the $C_2$–$C_3$ bonds of unsulfated uronic acids, by making glycosidic bonds of modified residues labile to alkali or, when reduced, to acid, as shown by the earlier investigation of Casu, B. "Structure and biological activity of heparin", Advance Carbohydr. Biochem., 43, 1985, Ac. Press, P. 51). The remnant is composed of a derivative of α, γ-dihydroxybutyric acid linked by acetalic bond with $C_1$ of amino sugar (Tab. I, reaction IV).

TAB. I.

End-terminals of oligosaccharide fractions obtained with different depolymerization processes.

Reaction I occurs according to this invention.

U.S. Pat. No. 4,281,108 describes a low molecular weight heparin which is obtained by N-desulfation through the intermediate heparamine, depolymerization, by heating in an acidic medium, with an oxidizing agent followed by re-sulfation.

This process creates deep alterations in the heparinic structure, which cannot be however be restored even by re-sulfation.

The oligosaccharides and/or oligosaccharide fractions of this invention are obtained by the process of the Patent application No. 921,332 which is a Continuation in Part of U.S. Ser. No. 582,933 and have an average molecular weight lower than 5,000 Daltons. These oligosaccharides and/or oligosaccharide fractions are obtained from heparin by means of depolymerization processes. A few proposals on processes involving free radicals and leading to depolymerization of polysaccharides have been made. The hydroxyl radical (HO.) has been found to be the most useful initiator of depolymerization. It can be generated, for example, by Fenton's reaction ($Fe^{++}$—$H_2O_2$), persulfate ion and systems based on oxygen, ascorbate and metal ions.

A process of depolymerization (Tab. I, reaction I) of heparin based on generation of free radicals HO. through divalent metal ions (such as $Cu^{++}$), hydrogen peroxide and ascorbic acid as described in the annexed FIG. 1 here below has been developed according to the U.S. Ser. No. 582,933 and its Continuation in Part No. 921,332. The oligosaccharide fractions of the present invention are designated herein as OP-125, OP L51184, OP-220, C 2181 I which have an average molecular weight ranging from 2100 to 3570 Daltons, OP 381/1/1 having an average molecular weight of 2000 Daltons, OP 119, C 2085 II having an average molecular weight of 1700 and OP 381/1/2 having an average molecular weight of 1000 Daltons. The generation of HO. occurs in a solution of heparin by adding a known amount of $H_2O_2$ in presence of 0.001–0.02 M cupric salt and at controlled pH and temperature, as described in U.S. Ser. No. 582,933 and in its Continuation in Part No. 921,332. Operative conditions described in the above-mentioned applications, such as pH, temperature, hydrogen peroxide addition rate and reaction times, have been further investigated.

The depolymerized products obtained in the tests have been isolated, analyzed in various assays and characterized. It has been found that little or no depolymerization takes place in the range of pH 3–5. As the pH is raised above 6, the extent of depolymerization increases markedly. Thus, the reaction is controlled by pH, temperature and reactions time. Different low molecular weight fragments endowed with specific activities have been obtained by carrying out chemical depolymerization and by varying the conditions of the process of the U.S. Ser. No. 582,933.

The anticoagulant activity of these fractions, quantified in APTT units (activated partial thromboplastin time units) and the whole blood anticoagulant activity and their specific antiprotease (antifactor Xa and antifactor IIa) actions have been determined (Basu and coll., New Eng. J. Med., 287, 324, 1972). These studies have demonstrated that a linear correlation exists between molecular weight and APTT, whereas a hyperbolic correlation between the molecular weight of chemically depolymerized heparin-fractions and their anti-factor Xa activity (AXa Units) or AXa/APTT has been observed as shown in FIG. 2. The anti Xa activity has been evaluated according to Teien A.N., (Thrombosis Res., 8, 413, 1976).

The molecular weights have been calculated using the HPLC technique with consecutive columns: Protein Pak 125 and Protein Pak 60 (Waters); Run conditions including eluent 0.125 M $Na_2SO_4$ and 2 nm $Na_2HPO_4$ at pH 6; Flow rate 0.9 ml/min; Detector: UV and refractive index.

The calibration curve has been plotted using authentic samples of natural heparin fractions which have been separated by gel filtration Chromatography on Sephacryl S-200 (Pharmacia), or Ultragel Ac.A 202 and Ultragel Ac.A 54 (LKB) columns. The molecular weights of the authentic samples have been assessed by electrophoresis on polyacrylamide by a standard method (Hilborn J. C. and coll., Anal. Biochem., 39, 80, 1974), by a reference viscosimetric method (Johnson E. A. and Mulloy B. B., Carbohydrate Res., 51, 119, 1976) and by analytical ultracentrifugation. In the depolymerization process no desulfation takes place, as shown by the test of total carboxyl and total sulfate groups and by calculation of the ratio $SO_3^-/COO^-$ prior to and after the depolymerization process. This ratio was deduced through potentiometric analysis (Mascellani G. et al., Il Farmaco, ed. Pr. 43, 161, 1988).

The fragments obtained by means of the process of this invention have been submitted to the 13C.NMR spectroscopy to detect the structure. The samples were solubilized in $D_2O$. The reported 13C.NMR chemical shifts regard external reference, tetramethylsilane. Methanol is used as internal reference. The methanol chemical shift in $D_2O$ in comparison with that of tetramethylsilane was 51.75 ppm according to the method described by Casu B. (Biochem. J., 197, 599, 1981). The 13C.NMR spectra of the depolymerized heparin products remained essentially the same as the spectrum of the parent heparin, indicating retention of the native structure. In addition, the NMR spectra of the typical depolymerized products exhibit two weak signals at 92.7 and 94.4 ppm due to reducing end groups of D-glucosamine N,6-disulfate (alpha-anomer) and L-iduronic acid 2-sulfate respectively.

These signals are one of the major distinguishing features of the depolymerized products obtained by a free radical depolymerization process, as from FIG. 3, unlike other oligosaccharides which are obtained through deaminative cleavage, according to, for instance, example 1 of U.S. Pat. No. 4,500,519. In the deaminative cleavage process peculiar signals indicating 2, 5-anhydromannose residue (mostly 6-0sulfate) are evident at 69.0 (am-6), 81.5 (am-5), 86.0 (am-2), 86.6 (am-4), 90.5 (am-1) ppm as shown in FIG. 3.

The gel permeation chromatographic (GPC) profile on HPLC and 13C.NMR spectra indicate that the process catalyzed by free radicals leads to cleavage of glycosidic bonds of both uronic acids and 2-sulfamino-2-deoxy-D-glycopyranose in heparin chains. On the contrary, the molecular weight distribution of the product LMWH obtained by nitrous acid cleavage according to U.S. Pat. Nos. 4,500,519 and 4,351,938 exhibits 600 Dalton discontinuous ranges of molecular weights instead of the continuous progressive distribution of the product according to the present application. These differences are clearly shown in FIG. 4.

The oligosaccharides of the present invention are fragments of heparin, having 6–12 saccharidic units and molecular weight from 3500 to 1700 Daltons. They have reducing end groups composed of glucosamine N, 6-disulfate and iduronic acid 2-sulfate (see FIG. 1). The structure is the same as in heparin unless the molecular weight.

The oligosaccharides are obtained by a radicalic process which is originated by HO., generated by a peroxide, for instance $H_2O_2$, the catalyst $Cu^{++}$ and ascorbic acid. The amount of HO. radicals is dependent on temperature, pH, reagent addition rate and reaction times. The depolymerization rate is dependent on concentration of heparin as well as on concentration of other inert quenchers of free radicals such as salt (NaCl, $CH_3COONa$). Therefore the process can be modulated as much as one likes and oligosaccharide fragments can be obtained by exhaustive depolymerization process.

The oligosaccharide of present invention have lost anticoagulant activity of heparin. They have antiatherosclerotic activity, antithrombotic activity in arterial as well as in venous thrombosis, good bioavailability by sub-cutaneous and by oral route and long lasting effect.

They inhibit platelet aggregation "ex vivo", induced by collagen, ristocetin and ADP. The parent heparin, on the contrary, induces platelet aggregation (Brace L. D., Fareed J., Seminars in Thromb. and Haemostas. 11, 190 (1985); Eika C., Scand. J. Haematol. 8, 248, 1972) and/or potentiates the platelet aggregation induced by other agents. The oligosaccharides reduces platelet adhesiveness.

The pharmacological results are predictive of the clinical usefulness of oligosaccharides of this invention administered in oral doses of 3-15 mg/Kg daily, or in injectable doses of 1-5 mg/Kg daily.

The present invention also concerns all the aspects, applicable on an industrial scale, associated with the use of the products, resulting from the invention, for human therapeutic applications such as antithrombotic, antiatherosclerotic, fibrinolytic agents, with very poor or no anticoagulant activity; for the purpose, the compounds, that are the object of the present invention, are formulated, by conventional techniques and excipients, as pharmaceutical compositions suited for parenteral, topical and oral administration.

Examples of formulations, suited for parenteral administration, include sterile solutions contained in ampuls.

Examples of formulations, suited for oral administration, include capsules, tablets and syrups, wherein the active ingredient may also be vehiculated in form of liposomes or micelles.

Examples of topical formulations are provided by ointments comprising the usual excipients known in the art.

The below reported examples illustrate the invention with no limitation to its scope.

EXAMPLE 1

Preparation of oligosaccharides fractions, Sample OP-2123 (according to the U.S. Ser. No. 582,933), now U.S. Pat. No. 4,629,699.

Commercial beef mucosa heparin with an average molecular weight of 15,000 Daltons exhibiting 170 APTT/mg and 172 AXaU/mg was subjected to depolymerization according to the process of U.S. Pat. No. 4,629,699. Ten grams of heparin were dissolved in 700 ml of an aqueous solution containing 30 g (500 m.moles) of sodium chloride and 30 g (200 m.moles) of Sodium acetate tri-hydrate ($CH_3COONa.3H_2O$). The pH was adjusted to 7.8 by means of 2N NaOH. First, 200 ml of an aqueous solution containing 3.5 g (20 m.moles) of ascorbic acid adjusted to pH 7-7.5 by means of 2N NaOH and then 100 ml of an aqueous solution containing 0.45 g (2.25 m.moles) of cupric acetate monohydrate were added, under constant stirring, to the resulting solution. Subsequently 15 ml of 36% hydrogen peroxide (180 m.moles) is added very slowly under stirring. The pH was constantly adjusted to 7.8 by means of 2N NaOH and the mixture was kept at 50° C. for 20 hours.

After concentration under vacuum to one-half the volume, an amount of 3% by weight, referred to the volume of the mixture, of EDTA sodium salt was added, the pH was adjusted to 6.5-7 and the product was precipitated by addition of two volumes of methanol. The product was purified by repeating twice the precipitation with methanol. This product is designated herein as OP-2123.

The yield by weight of the low molecular weight heparin product composed of oligosaccharides having an average molecular weight of 4500 Daltons was 81%.

EXAMPLE 2

Exhaustive depolymerization studies 25 g of heparin, previously depolymerized by the process of Example 1 according to U.S. Ser. No. 582,933 and having the following characteristics: (APTT U/mg=28; AXaU/mg=83; in vivo antithrombotic activity=116 Units; molecular weight=4300) was subjected to a process of further depolymerization, as described in the following.

25 g of the low molecular weight fraction was poured into 200 ml of water with 0.75 g of copper acetate and 8.75 g of sodium ascorbate. Then 180 ml of 16% hydrogen peroxide was slowly added under stirring during a period of two hours at 65°-70° C. The pH was kept at 7.4, by means of NaOH. The resulting solution, allowed to settle overnight, cooled at room temperture, adjusted to pH 6, was transferred on a Chelex 100 (R) column (2.8φ×13 cm), then on an amberlite (R) column (IRA. 400 OH-form, 4.2φ×8 cm) and subsequently on a polysturene column, strongly acid in the $H^+$ form.

The eluate was adjusted with NaOH to pH 7, and freeze-dried. The product 19.55 g (78% yield) was a low molecular weight heparin designated as OP 119. Its characteristics, compared with the starting product, are reported in the following table.

| Product | M.W. | S % | Uronic acids % | eq-$SO_3H$ / eq-COOH |
|---------|------|------|---------------|----------------------|
| OP 2123 | 4300 | 10.78 | 31.23 | 2.09 |
| LMW OP 119 | 1700 | | | 2.12 |

In spite of the reduction in molecular weight, the ratio $SO_3^-/COOH$ remains unchanged.

EXAMPLE 3

The oligosaccharide OP 125 has been obtained under the same conditions as Example 2 except for temperature which was 60° C.

EXAMPLE 4

The oligosaccharide OP L51184 has been prepared at 55° C. and pH 7.3, under the same conditions.

EXAMPLE 5

The OP 220 oligosaccharide has been performed under the conditions described in Example 2, but hydrogen peroxide addition time of 3.5 hours.

EXAMPLE 6 (OP 381/1/1)

300 g of heparin dissolved in 2 l of water and added with 12 g of monohydrate copper acetate is placed in a reactor.

During a period of 3.6 hours 1000 ml of 16% solution of hydrogen peroxide is added to the reaction mass, while pH is kept at 7.5 with N-Sodium hydroxide and the internal temperature is increased, by outside heating, during the first hour of reaction, from 44° C. to 66° C.

pH is adjusted to 5.5 with 120 ml of 30% acetic acid and 6 g of ascorbic acid are added. Oligosaccharides are cooled and precipitated with 3 volumes of methanol. After filtrating and drying 192.7 g of product having average molecular weight of 2900 Daltons is obtained. Filtrate A is set aside. 191 g of this intermediate product is dissolved in 1300 ml of water heated up to 68° C. 400 ml of 16% solution of hydrogen peroxide is added in 2.3 hours, at pH constantly kept at 7.5 with N-Sodium hydroxide.

J. Haematol. 7, 374, 1970) and does not cause thrombocytopenia.

These characteristics explain the surprising activity in the experimental model of arterial thrombosis of OP 381/1/1. OP 381/1/2

The filtrate A, set aside in the first part of this Example 6, is concentrated under vacuum to 10 1.3 volumes of acetone are added. The resulting precipitated is collected by filtration. The precipitate is 10% dissolved again in water and percolated in 100 ml of Chelex 100

TABLE II

Oligosaccharide structure - Activity characteristics

| | | | | | | ACTIVITIES | | | |
|---|---|---|---|---|---|---|---|---|---|
| | | | | IN VITRO | | IN VIVO (ED50 mg/kg) | | | |
| | | | | | | Art. Thromb. (5) | | Ven. Thromb. (6) | |
| Example | Sample | M.W.p (1) | $SO_3^-/COO^-$ (2) | U.APTT(3) | U.AXa(4) | i.v. | s.c. | i.v. | s.c. |
| 5 | OP 220 | 3570 | 2.18 | 4 | 58 | | | | |
| 8 | C 2081 I | 3500 | 2.19 | 2 | 57 | 3.3 | 3.6 | 0.4 | 1.8 |
| 4 | OP L51184 | 2880 | 2.21 | 3 | 48 | 2.6 | | | |
| 7 | C 2085 I | 2300 | 2.16 | 2 | 51 | 2 | 4.6 | 0.9 | 1.8 |
| 3 | OP 125 | 2100 | 1.9 | | | 1.6 | 4.9 | 1.0 | |
| 6 | OP 381/1/1 | 2000 | 2.2 | 1.5 | 30 | 1.5 | 5.9 | 1.0 | 2.1 |
| 7 | C 2085 II | 1700 | 2.2 | 0.7 | 9 | 2.1 | 4.8 | 1.2 | 5 |
| 2 | OP 119 | 1700 | 2.12 | 0.6 | 8 | 2.6 | | | |
| 6 | OP 381/1/2 | 1000 | | inactive | 2.8 | 12.2 | | 4.4 | 21 |
| | Heparin | 13500 | 2.22 | 170 | 172 | 1 | 8.0 | 0.2 | 4.5 |
| | LMW Heparin | 4500 | 2.19 | 30 | 78 | 2 | | 0.3 | |

(1) By HPLC;
(2) according to Mascellani G. et al. Il Farmaco, Ed. pr 43, 161, 1988;
(3) according to Basu et al. N. Engl. J. Med. 287, 324, 1972; according to Teien A.N. et al. Thromb. Res., 8, 413, 1976;
(5) according to Lavelle S.M. et al. in "Standardization of animal models of thrombosis", Proceedings Ang. Symp. Kitzbuhel, H.K. Breddin 1983, 157;
(6) according to Reyers et al. Thromb. Res., 18, 699, 1980.

After cooling, 4 volumes of methanol are added. The precipitate is collected by filtration and dried. An amount of 120 g of product is obtained. All the solid material is re-dissolved in water and percolated in a Chelex 100 resin column (Bio-Rad) ($\phi$4 cm, 35 cm high). 3 volumes of methanol are added to the percolate.

The precipitate is collected and dried. 99.51 g of product named OP 381/1/1 is obtained.

Figure 5:
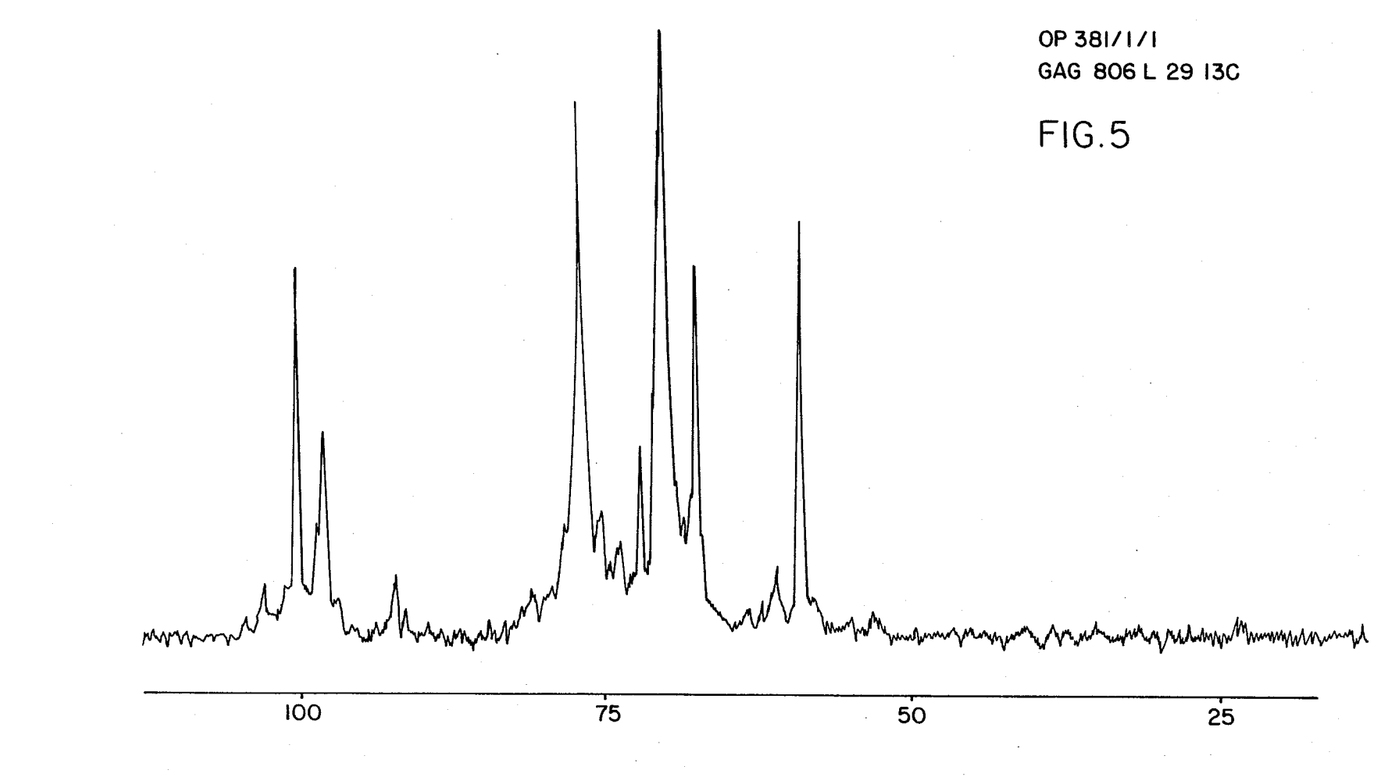

The 13C.NMR spectrum of the compound OP 381/1/1 (FIG. 5) shows the preservation of heparinic structure which remains essentially unchanged and the clear presence of signals $C_1$ of reducing anomeric carbons of iduronic acid and aminosugar. The compound undergoes biological in vivo and in vitro evaluation (Tab. II). It shows a surprising activity in experimental models of arterial thrombosis (Art. Thromb.) and venous thrombosis (Ven. Thromb.) in rat, good bioavailability and long lasting effect (up to 8 hours after treatment when administered by subcutaneous (s.c.) route). The ED50 s.c./ED50 i.v. ratio of the oligosaccharides of this invention is much more favourable than that of heparin. In the model of experimental thrombosis induced by kaolin in rat (Hladovec J., Physiol. Bohemoslovaca, 24, 551–554, 1975) i.v. ED50, s.c. Ed50 and per os Ed50 have resulted to be, respectively, 0.5 mg/kg, 3.6 mg/kg and 9.4 mg/kg. The ratio between these values (index of product bioavailability) is 1/7/19.

OP 381/1/1 at a 70 mcg/ml concentration inhibits platelet aggregation induced by 2 mcg of collagen. It inhibits the platelet aggregation by ristocetin, platelet aggregation (rabbit) induced by ADP at a concentration of 16 mcg/ml in comparison with heparin which, under the same conditions, increases ADP-induced aggregation by 20%. The product reduces platelet adhesiveness by 49% in comparison with normal saline (in "Adelplats" test, Mascia-Brunelli, Hellem A. J., Scand.

resin (Bio-Rad). The percolate, completely free of copper, is lyophilized. 15 g of OP 381/1/2 are obtained. The 13C.NMR of the compound OP 381/1/2 (FIG. 6) shows a typical signal dispersion of products having very low molecular weight (Casu B. et al. Biochem. J., 197, 599, 1981).

Figure 6:
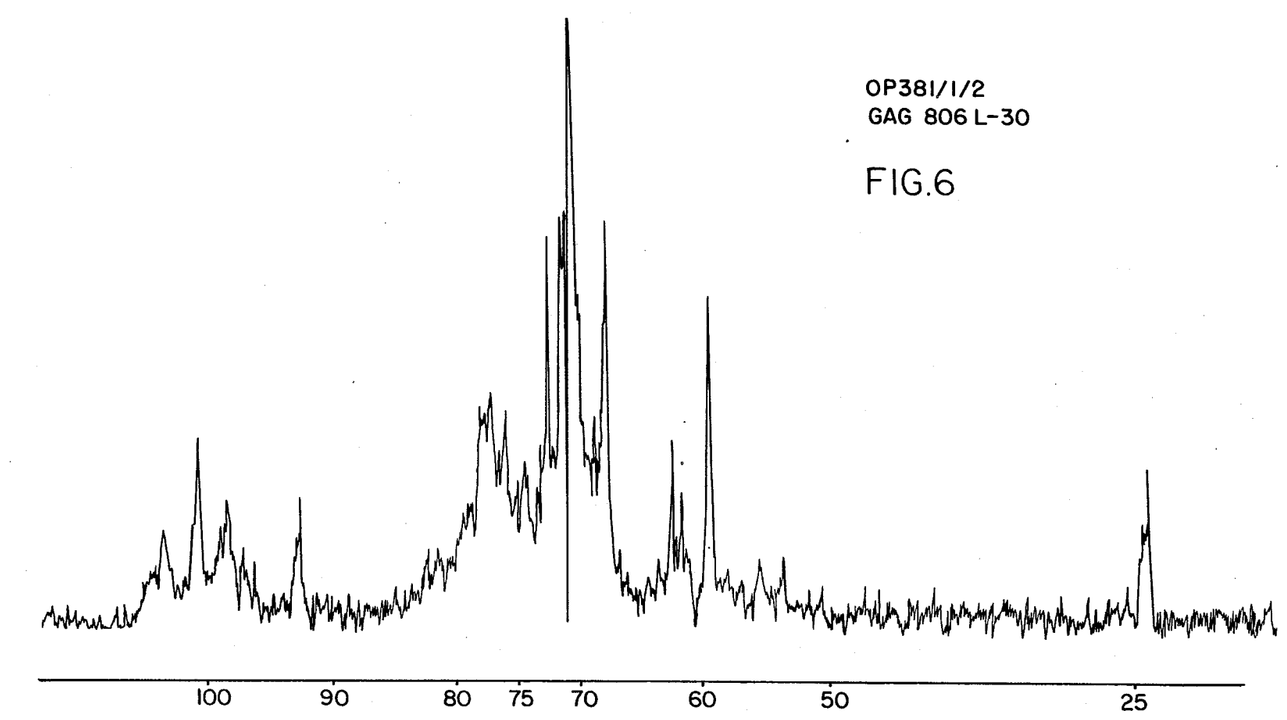

In comparison with heparins which are not depolymerized the anomers of glucuronic units are much more conspicuous. Reducing anomers as well are very strong, above all the one that corresponds to aminosugar sulfate. The general heparinic structure (shown in particular by the signals of sulfaminics and sulfate in $C_6$) has been maintained.

In the region of anomeric carbons also the presence of signals of $\beta$ anomers, generally disguised in heparins having higher molecular weight, is conspicuous.

EXAMPLE 7 (C 2085)

Fractionation on gel filtration column 5 g of the product OP 381/1/1, obtained in the Example 6, is added to 50 ml of 0.15 M NaCl solution and percolated in a column ($\phi$cm 5, 100 cm high) of Ultragel Ac.A 202 (LKB) at 2 ml/min. The 420 ml dead volume is eliminated and fractions of 10 ml each are collected. The first 30 fractions are discarded. The fractions from 31 to 104 (740 ml) are mixed (I). The other 112 fractions are mixed separately (II).

The two pools of fractions are concentrated until a small volume is obtained. They are desalted on Trisacryl GF 0.5 M and lyophilized. The products C 2085 I (3.1 g) and C 2085 II (0.47 g) are obtained.

EXAMPLE 8 (C 2081 I)

According to a process similar to that of Example 7, except that only the first 81 fractions are collected, the compound C 2081 I (1.04 g) is obtained.

The claims are:

1. An heparin fraction of molecular weight 2100–3570 which is a mixture of oligosaccharides containing an average of 6–8 monosaccharides, said oligosaccharides containing end groups composed of iduronic acid 2-sulfate or glucosamine N, 6-disulfate, said end group monosaccharides containing the reducing anomeric carbons, said oligosaccharides being constituted of multiples of monosaccharides.

2. The heparin fraction according to claim 1 wherein the $SO_3^-/COO^-$ ratio is essentially the same as in heparin.

3. Heparin fraction in accordance with claim 1 having molecular weight 2100–2300 and the same $SO_3^-/COO^-$ ratio as heparin.

4. The heparin fraction according to claim 1 which produces NMR signals at 92.7 and 94.4 ppm.

5. The heparin fraction according to claim 1 which is free of anticoagulant activity and which exhibits high antithrombotic activity in arterial thrombosis and venous thrombosis and which inhibits platelet aggregation.

6. A pharmaceutical composition with an antiatherosclerotic activity, anti-platelet aggregation activity and fibrinolytic activity, containing as the active ingredient the heparin fraction according to claim 1 in an amount sufficient to administer a dose of 3–15 mg/Kg daily, and excipients, in the form of capsules, tablets or syrups for oral administration.

7. A pharmaceutical composition with an antiatherosclerotic activity, anti-platelet aggregation activity and fibrinolytic activity, containing as the active ingredient the heparin fraction according to claim 1 in an amount sufficient to administer 1–5 mg/Kg daily in the form of a sterile solution, suitable for injection and excipients.

* * * * *